(12) United States Patent
Ebadollahi et al.

(10) Patent No.: US 8,996,443 B2
(45) Date of Patent: *Mar. 31, 2015

(54) SYSTEM AND METHOD FOR COMPOSITE DISTANCE METRIC LEVERAGING MULTIPLE EXPERT JUDGMENTS

(71) Applicant: International Business Machines Corporation, Armonk, NY (US)

(72) Inventors: Shahram Ebadollahi, White Plains, NY (US); Jimeng Sun, White Plains, NY (US); Fei Wang, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/033,801

(22) Filed: Sep. 23, 2013

(65) Prior Publication Data

US 2014/0025618 A1   Jan. 23, 2014

Related U.S. Application Data

(63) Continuation of application No. 13/070,084, filed on Mar. 23, 2011, now Pat. No. 8,566,268.

(60) Provisional application No. 61/391,321, filed on Oct. 8, 2010.

(51) Int. Cl.
| | | |
|---|---|---|
| G06F 17/00 | (2006.01) | |
| G06N 5/02 | (2006.01) | |
| G06N 99/00 | (2010.01) | |
| G06F 19/00 | (2011.01) | |
| G06N 5/04 | (2006.01) | |

(52) U.S. Cl.
CPC ............ *G06N 5/022* (2013.01); *G06N 99/005* (2013.01); *G06F 19/3443* (2013.01); *G06N 5/047* (2013.01)
USPC .......................................................... 706/48

(58) Field of Classification Search
None
See application file for complete search history.

(56) References Cited

U.S. PATENT DOCUMENTS

| | | |
|---|---|---|
| 5,774,576 A | 6/1998 | Cox et al. |
| 5,963,653 A | 10/1999 | McNary et al. |

OTHER PUBLICATIONS

Dwork, C., et al. "Rank Aggregation Methods for the Web" Proceedings of the Tenth International World Wide Web Conference, WWW'10. May 2001. pp. 613-622.

Lanckriet, G., et al. "Learning the Kernel Matrix With Semidefinite Programming" Journal of Machine Learning Research, vol. 5. Jan. 2004. pp. 27-72.

(Continued)

*Primary Examiner* — Alan Chen
(74) *Attorney, Agent, or Firm* — Tutunjian & Bitetto, P.C.; Louis J. Percello

(57) ABSTRACT

A system and method for a composite distance metric leveraging multiple expert judgments includes inputting a data distribution of multiple expert judgments stored on a computer readable storage medium. Base distance metrics are converted into neighborhoods for comparison, wherein each base distance metric represents an expert. The neighborhoods are combined to leverage the local discriminalities of all base distance metrics by applying at least one iterative process to output a composite distance metric.

20 Claims, 5 Drawing Sheets

(56) References Cited

OTHER PUBLICATIONS

Rahman, A., et al. "A Novel Confidence-Based Framework for Multiple Expert Decision Fusion" Proceedings of the British Machine Vision Conference 1998, BMVC 1998. pp. 205-213.

Sun, J., et al. "Localized Supervised Metric Learning on Temporal Physiological Data" 20th International Conference on Pattern Recognition, ICPR 2010. Aug. 2010. pp. 4149-4152.

Yang, L. "Distance Metric Learning: A Comprehensive Survey" Technical Report. Michigan State University. May 2006. pp. 1-51.

US 8,996,443 B2

SYSTEM AND METHOD FOR COMPOSITE DISTANCE METRIC LEVERAGING MULTIPLE EXPERT JUDGMENTS

RELATED APPLICATION INFORMATION

This application claims priority to provisional application Ser. No. 61/391,321 filed on Oct. 8, 2010, which is incorporated by reference herein in its entirety.

This application is a Continuation application of allowed co-pending U.S. patent application Ser. No. 13/070,084 filed on Mar. 23, 2011, incorporated herein by reference in its entirety.

BACKGROUND

1. Technical Field

The present invention relates to processing data, and more particularly to systems and methods for determining a composite distance metric between data from different sources.

2. Description of the Related Art

Distance metric learning is one of the most fundamental problems in data mining. Existing techniques aim at constructing a single distance metric directly from the data. However, in real applications, multiple base distance metrics may already exist. For example, in healthcare applications, different physicians may have different patient distance metrics in mind.

Distance Metric Learning (DML) is applicable in data mining and machine learning fields. Most DML algorithms are learned directly from the data. Depending on the availability of supervision information in the training data set (e.g., labels or constraints), a DML algorithm can be classified as unsupervised, or semi-supervised and supervised. In particular, supervised DML (SDML) constructs a proper distance metric that leads data from the same class closer to each other, while data from different classes are moved further apart from each other. In fact, SDML can be categorized as including global and local methods. A global SDML method attempts to learn a distance metric that keeps all data points within the same class close, while separating all data points from different classes far apart. Typical approaches in this category include Linear Discriminant Analysis (LDA) and its variants.

Although global SDML approaches achieve empirical success in many applications, it is difficult for a global SDML to separate data from different classes since the data distribution is usually very complicated (e.g., the data from different classes are entangled with each other). Local SDML methods, on the other hand, first construct local regions (e.g., neighborhoods around each data point) and, in each local region, attempts to pull data within the same class closer while pushing data in different classes further apart. Some representative algorithms include Large Margin Nearest Neighbor (LMNN) classifiers, Neighborhood Component Analysis (NCA) and Locality Sensitive Discriminant Analysis (LSDA). It is observed that these local methods can generally perform much better than global methods.

A related topic includes multiple kernel learning, which has been studied extensively in the machine learning and vision community. The goal in multiple kernel learning is to learn a strong kernel by integrating multiple weak kernels. In healthcare applications, multiple patient-patient kernel matrices are combined into a strong kernel to assess patient similarity. However, the practical difficulty of multiple kernel learning includes the following: 1) multiple kernel learning is not easy to generalize to new data points. For example, the existing similarity kernel will not be able to handle new patient arrivals until the kernel is recomputed to capture the new patient. 2) The computation complexity for multiple kernel learning is prohibitively expensive, often requiring a computational complexity of $O(N^3)$, where N is the number of data points. These challenges significantly limit the practical value of multiple kernel learning.

SUMMARY

In accordance with the present principles, a method for processing data includes inputting a data distribution of multiple expert judgments stored on a computer readable storage medium. Base distance metrics are converted from a plurality of sources into neighborhoods for comparison. Each base distance metric represents an expert. The neighborhoods are combined to leverage the local discriminalities of all base distance metrics by applying at least one iterative process to output a composite distance metric.

In accordance with the present principles, a system for processing data includes inputting a data distribution of multiple expert judgments stored on a computer readable storage medium into a neighborhood formulation module. The neighborhood formulation module is configured to convert base distance metrics from a plurality of sources into neighborhoods for comparison. Each base distance metric represents an expert. A neighborhood combination module is configured to combine the neighborhoods to leverage the local discriminalities of all base distance metrics by applying at least one iterative process to output a composite distance metric.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1:
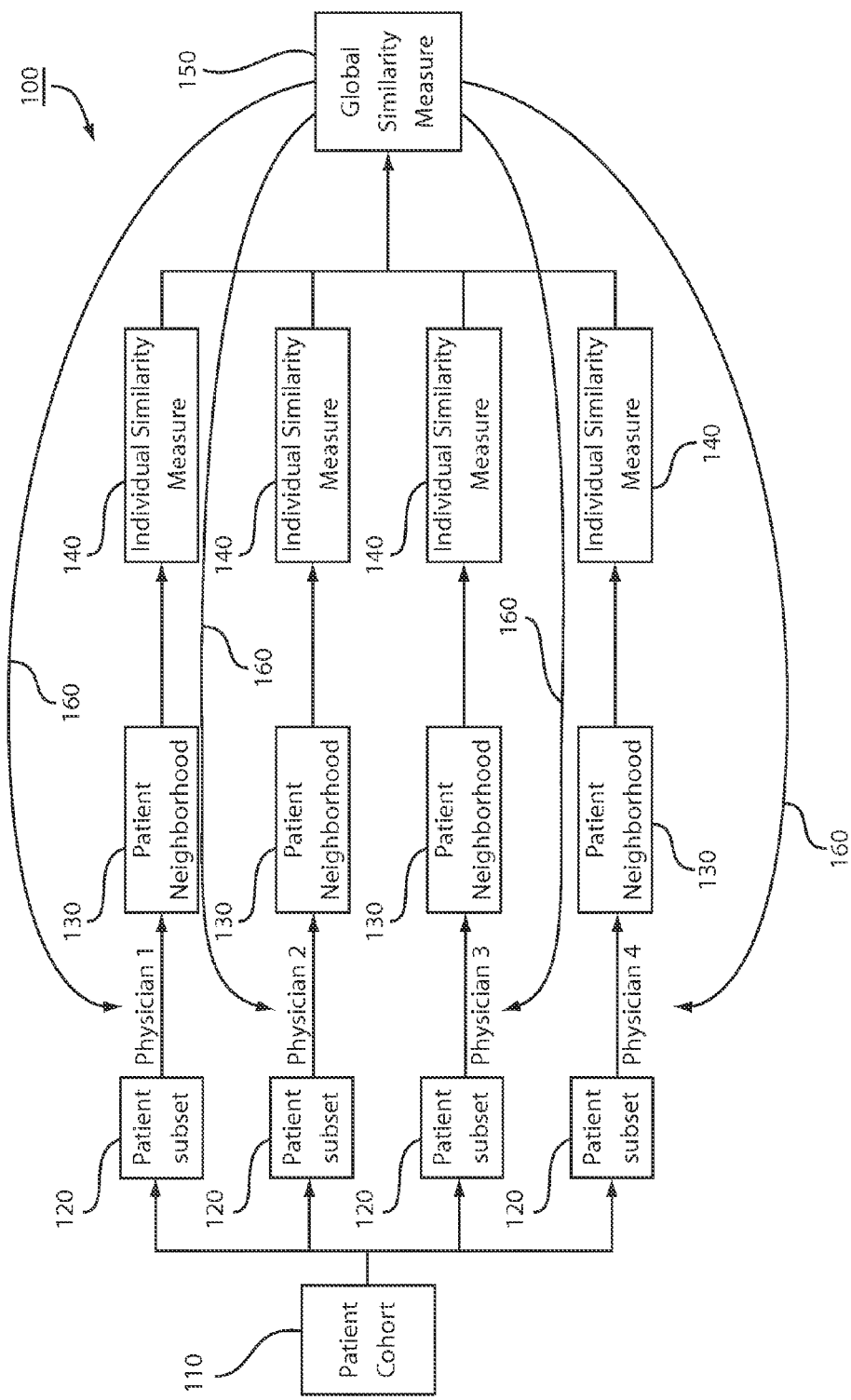
FIG. 1 is a graphical illustration of a Composite Distance Metric applied to the healthcare field in accordance with one embodiment.

The present principles provide a new notion of learning a composite distance metric from multiple expert inputs. For most existing approaches in distance metric learning, only one expert input is involved. However, in real world applications, different experts typically have different inputs. For example, different doctors may have different opinions as to the similarities between different patients. The present principles provide a system and method to incorporate multiple expert judgments to learn a proper distance metric.

Neighborhoods are created around each expert and a distance function is learned for each expert input providing the distances among data points in relation to the expert opinion by solving an optimization problem. For multiple expert inputs, a linear combination is constructed of all the objectives to be optimized on each input, which are then optimized together with the combination coefficients simultaneously. The present methods are (1) scalable to large scale data sets; (2) easily generalized to process different types of data (nonlinear, multilinear); and (3) able to incorporate new expert input and new data.

In one embodiment in accordance with the present principles, multiple kernel learning integrates distance metrics. In particular, given a set of data points, multiple Base Distance Metrics (BDM) with the same set of features are assumed (e.g., Lp distance with different p values, cosine similarity). For each BDM, a local nearest neighborhood is identified around each data point. Then, the Composite Distance Metric (CDM) learns a composite distance (e.g., a Mahalanobis distance) by combining the discriminative information of the different neighborhoods as a quadratic optimization problem. The optimization problem is solved using iterative methods to output a global similarity measure. In another embodiment, the CDM may be modified to handle nonlinear data distributions in a kernelized CDM. Similarly, in another embodiment, the CDM may also be modified to handle multilinear data distributions in a tensorized CDM.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Referring now to the drawings in which like numerals represent the same or similar elements and initially to FIG. 1, a block/flow diagram illustratively depicts one embodiment of a CDM applied in the healthcare field 100 in accordance with the present principles. An important problem in healthcare is how to find similar patients from a patient database from one query patient. Physicians often have their own perception of similarity based on their own patients and beliefs. A use case in the healthcare application includes a medical group with multiple physicians collectively serving a particular patient cohort.

In block 110, a patient cohort of the medical group is shown. The patient cohort is divided into subsets and assigned to a physician in blocks 120. In blocks 130, the CDM constructs a patient neighborhood around each physician, with the neighborhood representing the physician's judgments for each of the patients. Based on this neighborhood, an individual similarity measure for each physician is determined in blocks 140. The CDM will aggregate the individual similarity measures for all physicians to determine a global similarity measure in block 150. The global similarity measure 150 is provided back to each physician in feedback 160 so that each physician will be able to compare their individual similarity measure with the global similarity measure of the medical group. In another application, the CDM may be used to compare patient similarity by determining a distance between two patients.

It will be appreciated by one of ordinary skill in the art that the present principles are not restricted to the healthcare field. For example, in a computer repair business, a group of computer technicians may work together to serve a particular client base. The CDM can construct neighborhoods around each computer technician to create an individual similarity measure. The individual similarity measures can then be combined to determine a global similarity measure.

Figure 2:
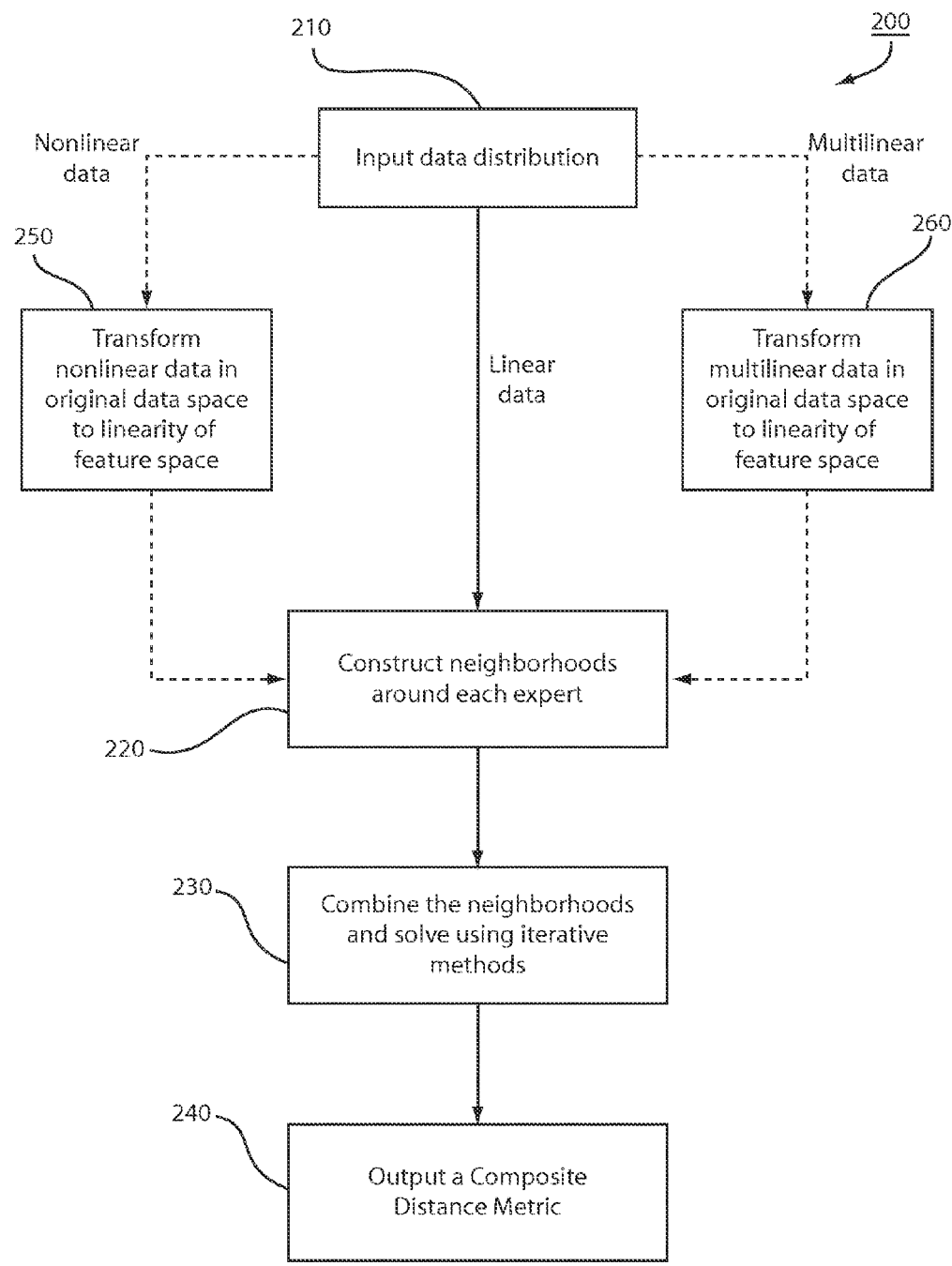
FIG. 2 is a block/flow diagram of a Composite Distance Metric method in accordance with one embodiment.

Referring now to FIG. 2, a block/flow diagram illustratively depicts one embodiment of a Composite Distance Metric (CDM) method 200 in accordance with the present principles. In block 210, a data distribution is inputted into the CDM. In a preferred embodiment, the data distribution is the constructed local compactness and scatterness matrices for each expert. It should be recognized that the dashed lines represent alternate embodiments in accordance with the present principles. In one embodiment, the inputted data distribution is nonlinear. In block 250, the nonlinear data distribution is transformed from the original data space to the linearity of the feature space. In another embodiment, the inputted data distribution is multilinear. In block 260, the multilinear data distribution is transformed from the original data space to the linearity of the feature space.

In block 220, neighborhoods are constructed around each expert from the data distribution. Block 220 is explained in further detail with respect to FIG. 3. In the healthcare application example, each physician represents a BDM and a neighborhood of patients is constructed around each physician. Each neighborhood represents the individual similarity measure of the physician. In block 230, the neighborhoods are combined by applying iterative methods. Block 230 is explained in further detail with respect to FIG. 4. In block 240, a composite distance metric is outputted. In the healthcare application example, the composite distance metric represents the global similarity measure of the medical group.

The CDM method will be explained in more detail below, however, in doing so, the framework of a Distance Metric Learning (DML) with local discrimination will be followed. Therefore, the DML with local discrimination will first be explained and then applied to the CDM. In presenting the DML with local discrimination, let $X=[x_1, \ldots, x_n] \in R^{d \times n}$ be the matrix containing n data points, where each column $x_i \in R^d$ represents the i-th data point. Let $y=[y_1, \ldots, y_n]^T \in R^n$ be the data label vector with $y_i \in \{1, 2, \ldots, C\}$ denoting the label $x_i$ and C denoting the number of classes. The goal is to find a Mahalanobis distance as follows:

$$d_\Sigma(x_i, x_j) = \sqrt{(x_i-x_j)^T \Sigma (x_i-x_j)}$$

where $\Sigma \in R^{d \times d}$ is a Symmetric Positive Semi-Definite (SPSD) matrix.

A neighborhood is identified around each data point and classified as either homogeneous or heterogeneous to provide for enhanced local discriminability. The homogeneous neighborhood of $x_i$, denoted as $\mathcal{N}_i^o$, is the $|\mathcal{N}_i^o|$-nearest data points of $x_i$ with the same label, where $|\mathcal{N}_i^o|$ is the size of $\mathcal{N}_i^o$. The heterogeneous neighborhood of $x_i$, denoted as $\mathcal{N}_i^e$, is the $|\mathcal{N}_i^e|$-nearest data points of $x_i$ with different labels, where $|\mathcal{N}_i^e|$ is the size of $\mathcal{N}_i^e$. The base distance metric is used to construct the neighborhood $\mathcal{N}_i^o$ and $\mathcal{N}_i^e$. Local compactness is applied to the homogeneous neighborhood of point $x_i$ as follows:

$$C_i = \sum_{j:x_j \in \mathcal{N}_i^o} d_\Sigma^2(x_i, x_j)$$

and local scatterness is applied to the heterogeneous neighborhood of point $x_i$ as follows:

$$S_i = \sum_{k:x_k \in \mathcal{N}_i^e} d_\Sigma^2(x_i, x_k).$$

The average distance between the heterogeneous neighborhoods and homogeneous neighborhoods are computed using the following trace difference criterion:

$$J = \sum_{i=1}^n (C_i - S_i).$$

An optimal distance metric is learned by maximizing the difference between the heterogeneous neighborhoods and homogeneous neighborhoods, which is achieved by minimizing the trace difference criterion. Optimizing a trace difference criterion has several advantages over optimizing a trace quotient criterion, as it is easy to manipulate, convex and avoids the singularity problem.

Incomplete Cholesky decomposition can be applied since $\Sigma$ is SPSD:

$$\Sigma = WW^T.$$

Then J can be expanded as $$J = \text{tr}(W^T(\Sigma_C - \Sigma_S)W)$$

where $\text{tr}(\bullet)$ is the trace of the matrix, and $$\Sigma_C = \sum_i \sum_{j:x_j \in \mathcal{N}_i^o} (x_i-x_j)(x_i-x_j)^T$$

$$\Sigma_S = \sum_i \sum_{k:x_k \in \mathcal{N}_i^e} (x_i-x_k)(x_i-x_k)^T$$

are the local compactness and scatterness matrices, respectively. Thus, a base distance metric can be converted into a local neighborhood and formulated as follows:

$$\min_{W:W^TW=I} \text{tr}(W^T(\Sigma_C - \Sigma_S)W) \quad (1).$$

The orthogonality constraint $W^TW=I$ is imposed to reduce the information redundancy among different dimensions of W. Under the Ky Fan Theorem, let $H \in R^{d \times d}$ be a symmetric matrix with eigenvalues $\lambda_1 \leq \lambda_2 \leq \ldots \lambda_d$ and corresponding eigenvectors $U=[u_1, u_2, \ldots, u_d]$. Then $$\lambda_1 + \lambda_2 + \ldots + \lambda_k = \min_{P^T P = I_k} tr(P^T H P) \qquad 5$$

and the optimal $P^* = [u_1, u_2, \ldots, u_k]$ subject to orthonormal transformation. Applying the Ky Fan Theorem to equation (1), the optimal W is obtained by $W^* = [w_1, w_2, \ldots, w_k]$ with $w_i \in R^d$ being the eigenvector of $\Sigma_C - \Sigma_S$, whose corresponding eigenvalue is the i-th smallest. The local neighborhood, formulated by equation (1), is parameterized by the projection matrix W.

Referring back to the CDM method, the framework of the DML with local discrimination will be followed as it applies to the CDM. Once the data distribution is inputted into the CDM, neighborhoods are constructed.

Figure 3:
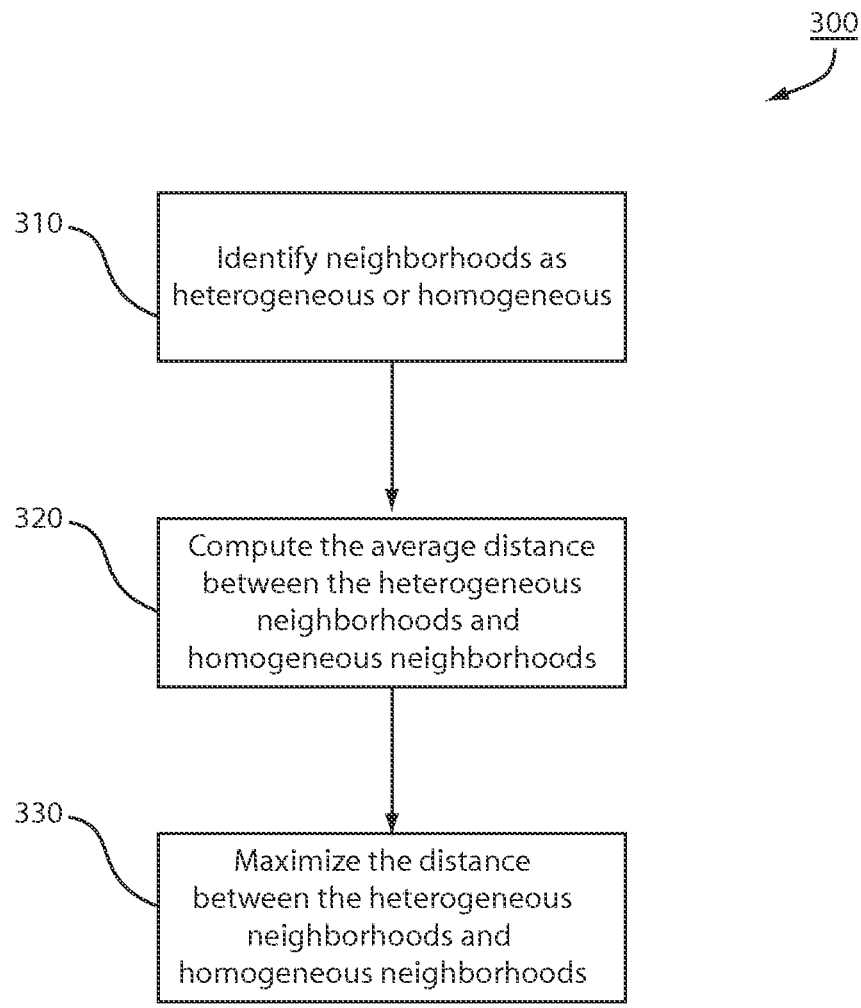
FIG. 3 is a block/flow diagram for converting multiple base distance metrics into neighborhoods in a Composite Distance Metric method in accordance with one embodiment.

Referring to FIG. 3, a block/flow diagram is depicted illustrating the construction of neighborhoods around each expert 300 in accordance with the present principles. In the healthcare application example, neighborhoods are constructed around each physician, where each physician is represented by a BDM and each neighborhood represents that physician's judgments with respect to their patient subset.

In block 310, neighborhoods are identified as either heterogeneous or homogeneous. In constructing the neighborhoods, the goal is still to learn a Mahalanobis distance as learned above. For the q-th BDM, a homogeneous neighborhood $\mathcal{N}_i^o(q)$ and a heterogeneous neighborhood $\mathcal{N}_i^e(q)$ are constructed for $x_i$. Correspondingly, a compactness matrix $\Sigma_C^q$ and scatterness matrix $\Sigma_S^q$ are constructed for the q-th BDM as follows:

$$\Sigma_C^q = \Sigma_i \Sigma_{j: x_j \in \mathcal{N}_i^o(q)} (x_i - x_j)(x_i - x_j)^T$$

$$\Sigma_S^q = \Sigma_i \Sigma_{k: x_k \in \mathcal{N}_i^e(q)} (x_i - x_k)(x_i - x_k)^T.$$

In block 320, the average distance between the heterogeneous neighborhoods and homogeneous neighborhoods is computed using the trace difference criterion, as performed above. In block 330, the average distance between the heterogeneous neighborhoods and homogeneous neighborhoods is maximized by minimizing the trace difference criterion. Each neighborhood can then be expressed as follows:

$$\min_{W: W^T W = I} tr(W^T(\Sigma_C^m - \Sigma_S^m)W).$$

In the healthcare application example, the above equation represents the individual similarity measure for each physician.

Minimizing the trace difference criterion over all BDMs results in the following:

$$J = \Sigma_{q=1}^m \alpha_q J_q = \Sigma_{q=1}^m \alpha_q tr(W^T(\Sigma_C^q - \Sigma_S^q)W)$$

where $\alpha_q$ is the combination coefficient for the q-th BDM, $\alpha$ is constrained to be in a simplex as $\alpha_q \geq 0$, $\Sigma_q \alpha_q = 1$, and m is the number of BDMs. By minimizing the trace difference criterion over all BDMs, the local discriminalities of all BDMs are leveraged to create a more powerful discriminative metric. The CDM is then formulated as the following optimization problem:

$$\min_{\alpha, W} \Sigma_{q=1}^m \alpha_q tr(W^T(\Sigma_C^q - \Sigma_S^q)W) + \lambda \Omega(\alpha)$$

s.t. $\alpha \geq 0, \alpha^T e = 1$ (2)

$W^T W = I$ where $\alpha = (\alpha_1, \alpha_2, \ldots, \alpha_m)^T$, $\Omega(\alpha)$ is some regularization term used to avoid trivial solutions, and $\lambda \geq 0$ is the tradeoff parameter. In particular, when $\lambda = \inf$, then $$\alpha_q = 1/m$$

for all q and when $\lambda = 0$, then $\alpha_q = 1$ for only the best BDM while all others have zero weight.

Referring again to FIG. 2, in block 230, the neighborhoods are combined and a CDM is solved for using iterative methods. In one embodiment, the combined neighborhoods are represented by the optimization problem of equation (2). As can be observed, the optimization problem of equation (2) includes two unknown variables, $\alpha$ and W. Although the optimization problem is not jointly convex with respect to both variables, it is convex with respect to one variable with the other fixed. Therefore, the optimization problem can be solved using iterative methods. In a preferred embodiment, the optimization problem is solved using alternating optimization by applying block coordinate descent.

Figure 4:
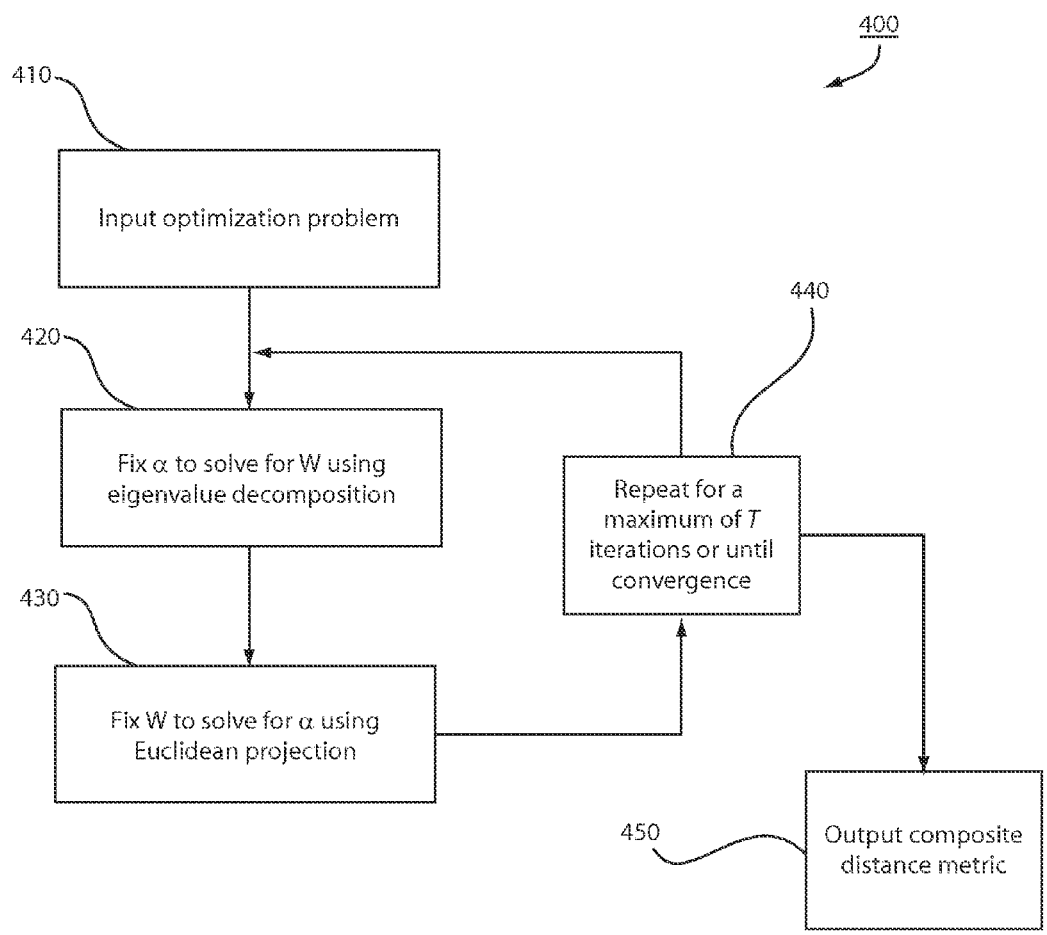
FIG. 4 is a block/flow diagram for combining neighborhoods by applying iterative methods in a Composite Distance Metric method in accordance with one embodiment.

In FIG. 4, the alternating optimization method 400 is illustratively depicted in accordance with one embodiment of the present principles. Equation (2) is solved by first solving for W with $\alpha$ fixed and then solving for $\alpha$ with W fixed. Alternating optimization is performed until a stopping criterion is reached. In a preferred embodiment, the stopping criterion includes either a maximum number of iterations or convergence. The maximum number of iterations is configured for T iterations, where T is a variable from 1 to t, a user defined input parameter. Convergence is established where the absolute value of the difference between the objective function loss in two consecutive steps is smaller than a threshold set by the user.

In block 410, an optimization problem is inputted into the alternating optimization method. If $\Omega(\alpha)$ is a convex regularizer with respect to $\alpha$, then the objective is convex with respect to $\alpha$ with W fixed and to W with $\alpha$ fixed. In block 420, $\alpha$ is fixed to solve for W. Starting at $\alpha = \alpha^0$, at step t, the optimization problem is solved for $W^{(t)}$ with $\alpha$ fixed at $\alpha = \alpha^{(t-1)}$ using eigenvalue decomposition as follows:

$$\min_W \Sigma_{q=1}^m \alpha_q^{(t-1)} tr(W^T(\Sigma_C^q - \Sigma_S^q)W) + \lambda \Omega(\alpha)$$

s.t. $W^T W = I$ (3).

Since the second term of the objective is irrelevant with respect to W, it can be discarded. The first term of the objective can then be rewritten as follows:

$$\Sigma_{q=1}^m \alpha_q^{(t-1)} tr(W^T(\Sigma_C^q - \Sigma_S^q)W) = tr(W^T[\Sigma_q^m \alpha_q^{(t-1)}(\Sigma_C^q - \Sigma_S^q)]W).$$

Considering the orthogonality constraint $W^T W = I$, the Ky Fan Theorem can be applied to solve equation (3) for $W(t) = [w_1^{(t)}, w_2^{(t)}, \ldots, w_k^{(t)}]$, with $w_i^{(t)}$ being the eigenvector of $E^{(t-1)} = \Sigma_q^m \alpha_q^{(t-1)}(\Sigma_C^q - \Sigma_S^q)$ whose eigenvalue is the i-th smallest. The computational complexity is $O(d^3)$, which is dominated by the eigenvalue decomposition.

In block 430, once $W^{(t)}$ is determined at step t, $\alpha$ is then solved for with W fixed. In one embodiment, $\alpha^{(t)}$ is determined by solving the following optimization problem:

$$\min_\alpha \Sigma_{q=1}^m \alpha_q tr((W^{(t)})^T(\Sigma_C^q - \Sigma_S^q)W^{(t)}) + \lambda \Omega(\alpha)$$

s.t. $\alpha \geq 0, \alpha^T e = 1$ (4)

where e is all one vector. To solve the optimization problem of equation (4), different choices of $\Omega(\alpha)$ are evaluated. For notational convenience, let $w^{(t)}=(w_1^{(t)}, w_2^{(t)}, \ldots, w_m^{(t)})^T$ with $w_i^{(t)} = \text{tr}((W^{(t)})^T (\Sigma_C^q - \Sigma_S^q) W^{(t)})$.

The optimization problem of equation (4) is first evaluated using L2 norm regularization, where $\Omega(\alpha) = \|\alpha\|_2^2$. Here, $\|\alpha\|_2^2 = \alpha^T \alpha$ is applied, which is a common regularizer, so that the optimization problem of equation (4) can be rewritten as follows:

$$\min_\alpha \alpha^T w^{(t)} + \lambda \|\alpha\|_2^2$$

s.t. $\alpha \geq 0, \alpha^T e = 1$.

The above result is a standard Quadratic Programming problem and can be solved by numerous mature software programs. However, since solving a Quadratic Programming problem can be time consuming, the problem is reformulated, for efficiency, to the following:

$$\alpha^T w^{(t)} + \lambda \|\alpha\|_2^2 = \left\| \sqrt{\lambda} \alpha + \frac{1}{\sqrt{2\lambda}} w^{(t)} \right\|_2^2 + \frac{1}{2\lambda} (w^{(t)})^T w^{(t)}.$$

Since the second term is irrelevant with respect to $\alpha$, it can be discarded and the optimization problem rewritten as follows:

$$\min_\alpha \|\alpha - \tilde{w}^{(t)}\|_2^2$$

s.t. $\alpha \geq 0, \alpha^T e = 1$ where $$\tilde{w}^{(t)} = \frac{1}{\sqrt{2\lambda}} w^{(t)}.$$

Therefore, the optimization problem turns into a Euclidean projection problem under the simplex constraints with L2 norm regularization.

The problem with L2 regularization is that it tends to uniformly select all base distance metrics, which may introduce some redundancies. Therefore, the optimization problem of equation (4) is evaluated using L1 norm regularization, where $\Omega(\alpha) = \|\alpha\|_1$. Here, $\|\alpha\|_1 = \sum_{q=1}^m |\alpha_q|$, which is a common regularizer, is applied to enforce a sparsity penalty on $\alpha$, such that the smaller $\|\alpha\|_1$ is, the sparser $\alpha$ will be. The optimization problem of equation (4) can be rewritten to the following:

$$\min_\alpha \alpha^T w^{(t)} + \lambda \|\alpha\|_1$$

s.t. $\alpha \geq 0, \alpha^T e = 1$.

The optimal solution to $\alpha^*$ is expected to have only non-zero entries whose corresponding base distance metrics are highly discriminative. However, with the nonnegativity and sum-to-one constraints, $\|\alpha\|_1$ is already restricted to 1, which makes the L1 regularization meaningless in this case. Therefore, either the L1 regularization or the sum-to-one constraint can be dropped. If the sum-to-one constraint is dropped, the optimal solution would be an all-zero vector, which is trivial. If the L1 regularization term is dropped, the optimal solution becomes:

$$\alpha_i^* \begin{cases} 1, & w_i^t = \min(w_1^{(t)}, w_2^{(t)}, \ldots, w_m^{(t)}) \\ 0, & \text{otherwise} \end{cases}$$

which only selects the most discriminative base distance metric and is, therefore, overly sparse.

Alternatively, a hybrid approach can be adopted. The optimization problem of equation (4) is evaluated using elastic net regularization, where $\Omega(\alpha) = \lambda_1 \|\alpha\|_2^2 + \lambda_2 \|\alpha\|_1$. Here, $\lambda_1 > 0$ and $\lambda_2 > 0$ are regularization constants. The elastic net regularizer can be viewed as a tradeoff between the nonsparse L2 norm regularization and sparse L1 norm regularization. The optimization problem can be rewritten as:

$$\alpha^T w^{(t)} + \lambda_1 \|\alpha\|_2^2 + \lambda_2 \|\alpha\|_1 =$$

$$\left\| \sqrt{\lambda_1} \alpha + \frac{1}{\sqrt{2\lambda_1}} w^{(t)} \right\|_2^2 + \lambda_2 \|\alpha\|_1 - \frac{1}{2\lambda_1} (w^{(t)})^T w^{(t)}.$$

Since the third term is irrelevant with respect to $\alpha$, it can be discarded and the problem simplified to:

$$\min_\alpha \|\alpha - \hat{w}^{(t)}\|_2^2 + \lambda_2 \|\alpha\|_1$$

where $$\hat{w}^{(t)} = \frac{1}{\sqrt{2\lambda_1}} w^{(t)}.$$

As can be observed, the sum-to-one constraint and L1 norm regularizer are still redundant in this case and, therefore, one can be dropped. If the L1 norm regularizer is dropped, the problem becomes the same as L2 regularization. If the sum-to-one constraint is dropped, the problem becomes a nonnegative least absolute shrinkage and selection operator (LASSO) problem and can be solved by standard methods.

Evaluating the optimization problem of equation (4) for different choices of $\Omega(\alpha)$, L2 regularization using Euclidean projection is sufficient with a computational complexity of $O(m)$. Referring again to FIG. 4, in block 440, the optimization problem is repeatedly solved until a stopping criterion is met. The variables $W^{(t)}$ and $\alpha^{(t)}$ are solved for, with $\alpha$ representing the combination weight and W representing the projection matrix. The composite distance metric is represented by projection matrix W. The combination weight $\alpha$ represents the weight of each BDM. In FIG. 4, block 450 and FIG. 2, block 240, the composite distance metric is outputted.

In the healthcare application example, the output of the CDM is represented by projection matrix W. Patient similarity may be determined for two patients, each represented by a feature vector $v_1$ and $v_2$, respectively. A Mahalanobis distance between the two vectors is determined using precision matrix $W^T W$ as follows:

$$(v_1 - v_2)(v_1 - v_2)^T W W^T.$$

New feature vectors and new base distance metrics may be incorporated to adjust the distance of the CDM. New feature vectors are first absorbed into each base distance metric through a distance updating process, i.e., all base distance metrics are recomputed by adding the new feature. The new neighborhoods will be reconstructed and the composite distance will be relearned afterwards. New base distance metrics are converted into neighborhoods with an initial weight of zero. Alternating optimization will then be performed to further update the weights of all the BDMs.

One potential issue in applying the CDM is that the projected dimensionality k of matrix W needs to be predefined. Because there is no prior knowledge of the data distribution set, the projected dimensionality k is difficult to predefine. However, under the Ky Fan theorem, the optimal objective value of the optimization problem expressed in equation (3) is the sum of the smallest k eigenvalues of $E^{(t-1)}$. Therefore, k can be set to the number of negative eigenvalues of $E^{(t-1)}$.

As should be appreciated by one of ordinary skill in the art, the above-described CDM is one exemplary embodiment in accordance with the present principles. In other embodiments, the CDM may be modified to make it more effective and efficient for particular applications. In particular, where the data distribution consists of high dimensional data (e.g., text data), the data vectors $\{x_i\}_{i=1}^n$ are typically sparse, which will make the compactness matrix $\Sigma_C^q$ and scatterness matrix $\Sigma_S^q$ sparse, and the resultant matrix $E^{(t)}$ may also be sparse. As only the eigenvectors corresponding to the smallest k eigenvalues of $E^{(t)}$ need be found, faster iterative methods may be applied, such as the Lanczon algorithm, which would improve computational complexity from $O(d^3)$ to $O(dk^2)$.

In another embodiment in accordance with the present principles, the CDM may also be modified to handle new information. In dealing with new data from the population x, such as new patient data, it is projected into the feature space as follows:

$$\tilde{x} = W^T x.$$

In this way, the Mahalanobis distance of x is projected into the feature space as a Euclidean distance $d(\tilde{x}, \cdot)$. The new expert input information is equivalent to adding a new BDM, which will first be transformed into a neighborhood with an initial weight of zero. Next, alternating optimization is applied by solving for $\alpha^{new}$ by fixing $W = W^{old}$ and then solving for $W^{new}$ iteratively. Alternating optimization is performed until a stopping criterion is met. The composite distance metric is then outputted, represented by projection matrix W.

In another embodiment in accordance with the present principles, the CDM method is modified for nonlinear data distributions. A limitation of CDM is that it assumes a linear transform W to map the data points to a feature space so that the Euclidean distance in that feature space is the Mahalanobis distance in the original space. However, since most data distributions are nonlinear in nature, such a linear transform may not be optimal. Therefore, the CDM can be modified to create a kernelized composite distance metric.

The kernelized CDM method is similar to the CDM method outlined in FIG. 2, however, as illustrated in block 250, the data distribution is transformed to the linearity of the feature space. In particular, the data points are mapped from a high (possibly infinite) dimensional feature space via $\phi: R^d \rightarrow F$ to transform the nonlinearity in the original data space to the linearity in the feature space. More concretely, let $\phi(x_i)$ be the image of $x_i$ and $\Phi = [\phi(x_1), \phi(x_2), \ldots, \phi(x_n)]$ be the image of the original data matrix X. The goal is to learn the following Mahalanobis distance metric:

$$d_{\Sigma^\phi}(x_i, x_j) = \sqrt{(\phi(x_i) - \phi(x_j))^T \Sigma^\phi (\phi(x_i) - \phi(x_j))}.$$

Similar to CDM, incomplete Cholesky decomposition can be applied to factorize $\Sigma^\phi$ as follows:

$$\Sigma^\phi = W^\phi W^{\phi T}$$

where $W^\phi = [w_1^\phi, w_2^\phi, \ldots, w_k^\phi]$ is a low rank matrix, playing a similar role as W plays in CDM. To learn $W^\phi$ in the feature space F, the following optimization problem is solved:

$$\min_{\alpha, W^\phi} \Sigma_{q=1}^m \alpha_q \mathrm{tr}(W^{\phi T}(\Sigma_C^q - \Sigma_S^q)W^\phi) + \lambda \Omega(\alpha)$$

s.t. $\alpha \geq 0, \alpha^T e = 1$ (5)

$$W^{\phi T} W^\phi = 1$$

where $\Sigma_C^{\phi q}$ and $\Sigma_S^{\phi q}$ are the compactness matrix and scatterness matrix in the feature space, as defined as:

$$\sum_C^{\phi q} = \sum_i \sum_{j: x_j \in N_i^0(q)} (\phi(x_i) - \phi(x_j))(\phi(x_i) - \phi(x_j))^T$$

$$\sum_S^{\phi q} = \sum_i \sum_{k: x_k \in N_i^e(q)} (\phi(x_i) - \phi(x_k))(\phi(x_i) - \phi(x_k))^T.$$

Under the Representer Theorem, $W^\phi$ is extended to the following:

$$W^\phi = \Phi Y$$

where $Y = [\gamma_1, \gamma_2, \ldots, \gamma_k]$ and $w_i^\phi = \Phi \gamma_i$. Then:

$$W^{\phi T} \sum_C^{\phi q} W^\phi = \gamma^T \Phi^T \left[ \sum_i \sum_{j: x_j \in N_i^0(q)} (\phi(x_i) - \phi(x_j))(\phi(x_i) - \phi(x_j))^T \right] \Phi \gamma$$

$$= \gamma^T \left[ \sum_i \sum_{j: x_j \in N_i^0(q)} (K_i - K_j)(K_i - K_j)^T \right] \gamma$$

$$= \gamma^T \Xi_C^q \gamma$$

where a kernel matrix $K \in R^{n \times n}$ is defined with its (i,j)-th entry $K_{ij} = \phi(x_i)^T \phi(x_j)$, $K_i$ denotes the i-th column of K, and $$\Xi_C^q = \sum_i \sum_{j: x_j \in N_i^0(q)} (K_i - K_j)(K_i - K_j)^T.$$

Similarly, the Representer Theorem is used to find the following:

$$W^{\phi T} \Sigma_S^{\phi q} W^\phi = Y^T \Xi_S^q Y$$

where $$\Xi_S^q = \sum_i \sum_{j: k \in N_i^0(q)} (K_i - K_k)(K_i - K_k)^T.$$

The objective of the optimization problem of equation (5) can then be rewritten into the following:

$$\sum_{q=1}^m \alpha_q \mathrm{tr}\left( W^{\phi T} \left( \sum_C^q - \sum_S^q \right) W^\phi \right) + \lambda \Omega(\alpha) = \sum_{q=1}^m \alpha_q \mathrm{tr}(\gamma^T (\Xi_C^q - \Xi_S^q) \gamma) \lambda \Omega(\alpha)$$

and the orthogonality constraint of $W^\phi$ becomes:

$$W^{\phi T} W^\phi = Y^T \Phi^T \Phi Y = Y^T K Y.$$

The optimization problem of the kernelized CDM can then be rewritten as follows:

$$\min_{\alpha, Y} \Sigma_{q=1}^m \alpha_q \mathrm{tr}(Y^T (\Xi_C^q - \Xi_S^q) Y) + \lambda \Omega(\alpha)$$

s.t. $\alpha \geq 0, \alpha^T e = 1$ (6).

$$Y^T K Y = I$$

The optimization problem can be solved using alternating optimization, as in CDM. The optimization problem is convex with respect to Y or $\alpha$ with $\alpha$ or Y fixed, respectively, if $\Omega(\alpha) = \|\alpha\|_2^2$ is chosen under L2 norm regularization.

In solving the optimization problem of equation (6) by first fixing Y, the problem of solving α becomes a quadratic programming problem, as it was in CDM. However, to solve Y by fixing $\alpha=\alpha^{(t-1)}$, the optimization problem is rewritten as follows:

$$\min_Y \sum_{q=1}^m \alpha_q^{(t-1)} tr(Y^T(\Xi_C^q - \Xi_S^q)Y)$$

s.t. $Y^T K Y = I$.

The regularization term of the objective was discarded as it is irrelevant with respect to Y. To solve the optimization problem, let:

$$\Theta_q^{(t-1)} = \sum_{q=1}^m \alpha_q^{(t-1)}(\Xi_C^q - \Xi_S^q).$$

The optimization problem can then be simplified to:

$$\min_Y tr(Y^T \Theta_q^{(t-1)} Y)$$

s.t. $Y^T K Y = I$.

Since K is positive semi-definite, it can be factorized as the following:

$$K = U^T \Lambda U$$

where $\Lambda$ is a diagonal matrix with all positive eigenvalues of K on its diagonal line and U is stacked by their corresponding eigenvectors. By letting $\tilde{Y} = \Lambda^{1/2} U Y$, the optimization problem becomes:

$$\min_{\tilde{Y}} tr(\tilde{Y}^T \Lambda^{-1/2} U \Theta_q^{(t-1)} U^T \Lambda^{-1/2} \tilde{Y})$$

s.t. $\tilde{Y}^T \tilde{Y} = I$.

The solution of the optimization problem can be determined by applying the Ky Fan theorem, which states that the optimal $\tilde{Y}$ should be stacked by the eigenvectors of:

$$\tilde{\Theta} = \Lambda^{-1/2} U \Theta_q^{(t-1)} U^T \Lambda^{-1/2}$$

corresponding to its smallest k eigenvalues, and $$Y = U^T \Lambda^{-1/2} \tilde{Y}.$$

As in CDM, the alternating optimization method of kernelized CDM is repeated until a stopping criterion is met. The composite distance metric is then outputted.

In another embodiment in accordance with the present principles, the CDM is modified for multilinear data, such as image, EEG, and fMRI data. In this Tensorized CDM, data is presented as a multidimensional array (i.e., tensors) and a CDM for tensors is learned. The tensorized CDM method is similar to the CDM method illustrated in FIG. 2, however, as illustrated in block 260, the multilinear data is transformed to the linearity of the feature space. Specifically, the data matrix x is projected as $y = x \times_1 U_1 \times_2 U_2 \times \ldots \times_M U_M$, where M is the number of dimensions and neighborhoods are constructed similar to that as in the CDM method. The optimization problem can then be formulated as follows:

$$\min_{\alpha, \{U_i\}_{i=1}^K} \sum_{q=1}^m \alpha_q \sum_i \left( \sum_{x_j \in N_i^0(q)} \|y_j - y_i\|_F^2 - \sum_{x_k \in N_i^e(q)} \|y_k - y_i\|_F^2 \right) + \lambda \Omega(\alpha) \quad (7)$$

s.t. $\forall i = 1, \ldots, K, U_i^T U_i = I$ $\alpha^T e = 1, \alpha \geq 0.$

Let $Y_i^K$ be the mode K unfolding of $y_i$. The mode K compactness and scatterness matrices for the q-th BDM can then be defined as follows:

$$\Sigma_{C_q}^K = \sum_i \sum_{j: X_j \in} \mathcal{N}_{i^0(q)}(U_K Y_i^K - U_K Y_j^K)(U_K Y_i^K - U_K Y_j^K)^T$$

$$\Sigma_{S_q}^K = \sum_i \sum_{j: X_j \in} \mathcal{N}_{i^e(q)}(U_K Y_i^K - U_K Y_j^K)(U_K Y_i^K - U_K Y_j^K)^T.$$

The optimization problem is solved for α and $U_K$ for each dimension K as follows:

$$\min_{U_K^T U_K = 1} \sum_{q=1}^m \alpha_q tr\left( U_K^T \left( \sum_{C_q}^K - \sum_{S_q}^K \right) U_K \right).$$

The above formulation suggests that $U_K$ can be obtained by stacking the eigenvectors of $$\sum_{q=1}^m \alpha_q \left( \sum_{C_q}^K - \sum_{S_q}^K \right)$$

corresponding to its smallest k eigenvalues with α fixed. Then, α can be obtained by solving problem (7) when solving for all $U_K$ and all $y_i$. This procedure will be repeated iteratively until the stopping criterion is met.

Figure 5:
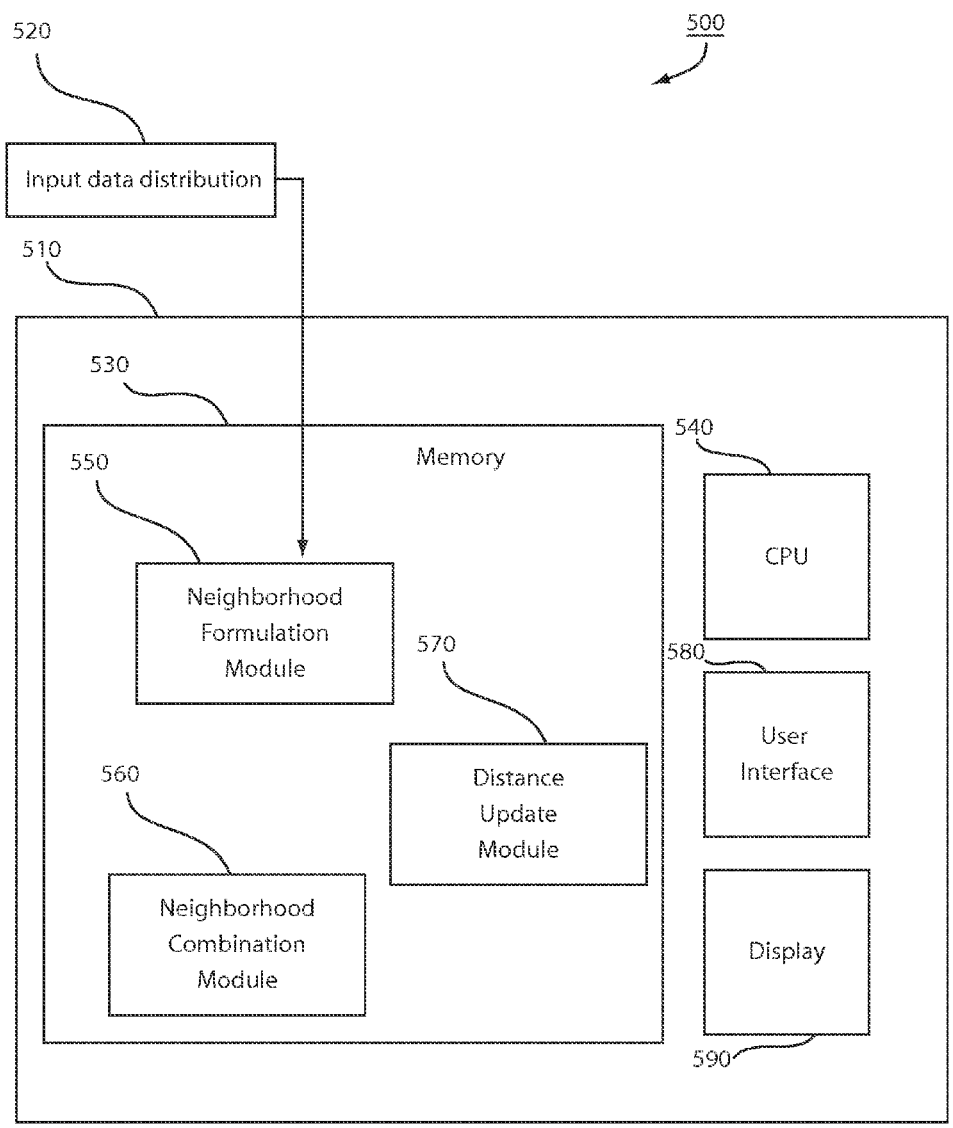
FIG. 5 is a block/flow diagram of a Composite Distance Metric system in accordance with one embodiment.

FIG. 5 illustratively depicts a block/flow diagram of a composite distance metric system 500 in accordance with one embodiment of the present principles. In block 520, a data distribution is inputted into the composite distance metric system 510. The composite distance metric system 510 includes memory 530, CPU 540, user interface 580 and display 590, which interface with all components of the composite distance metric system 510. Neighborhood formulation module 550, neighborhood combination module 560 and distance update module 570 are stored within memory 530. Data distribution 520 may also be stored within memory 530. User interface 580 may be configured to accept a number of user inputs, including the inputted data distribution, the maximum number of iterations or the threshold for convergence.

Neighborhood formulation module 550 converts the base distance metrics into neighborhoods for comparison. In a preferred embodiment, the neighborhoods include heterogeneous and homogeneous neighborhoods. Neighborhood formulation module 550 performs the method detailed in FIG. 3. Neighborhood combination module 560 combines the neighborhoods created in neighborhood formulation module 550 to learn the combination weights and low-dimensional representation of the input feature vectors. In a preferred embodiment, neighborhoods are combined using iterative methods, including alternating optimization. In one embodiment in accordance with the present principles, distance update module 570 is included to adjust the CDM to incorporate new feature vectors and base distance metrics.

Having described preferred embodiments of a system and method for a Composite Distance Metric leveraging multiple expert judgments (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for processing data, comprising:
  converting base distance metrics from a plurality of sources into neighborhoods for comparison, wherein each base distance metric represents an expert; and
  combining the neighborhoods to leverage the local discriminalities of all base distance metrics using a processor by applying at least one iterative process to output a composite distance metric.

2. The method as recited in claim 1, further comprising:
  adjusting the composite distance metric to incorporate a new feature vector or a new base distance metric.

3. The method as recited in claim 1, wherein the neighborhoods are identified as a homogeneous neighborhood or a heterogeneous neighborhood.

4. The method as recited in claim 3, wherein:
  the homogeneous neighborhood includes the nearest neighbors, based on input neighbor size, with a same input label; and
  the heterogeneous neighborhood includes the nearest neighbors, based on input neighbor size, with a different input label.

5. The method as recited in claim 1, wherein the iterative process includes alternating optimization.

6. The method as recited in claim 5, wherein alternating optimization includes eigenvalue decomposition and Euclidean projection.

7. The method as recited in claim 1, wherein:
  an individual similarity measure is determined for each expert; and
  the composite distance metric is provided back to each expert to compare to the individual similarity measure.

8. The method as recited in claim 1, wherein a similarity measure between a first patient with a first vector and a second patient with a second vector is determined by computing a Mahalanobis distance between the first vector and the second vector.

9. The method as recited in claim 1, wherein the data distribution is a multilinear data distribution.

10. A system for processing data, comprising:
  a neighborhood formulation module configured to convert base distance metrics from a plurality of sources into neighborhoods for comparison, wherein each base distance metric represents an expert; and
  a neighborhood combination module, having a processor, configured to combine the neighborhoods to leverage the local discriminalities of all base distance metrics by applying at least one iterative process to output a composite distance metric.

11. The system as recited in claim 10, further comprising:
  a distance update module configured to adjust the composite distance metric to incorporate a new feature vector or a new base distance metric.

12. The system as recited in claim 10, wherein the neighborhoods are identified as a homogeneous neighborhood or heterogeneous neighborhood.

13. The system as recited in claim 12, wherein:
  the homogeneous neighborhood includes the nearest neighbors, based on input neighbor size, with a same input label; and
  the heterogeneous neighborhood includes the nearest neighbors, based on input neighbor size, with a different input label.

14. The system as recited in claim 10, wherein the iterative process includes alternating optimization.

15. The system as recited in claim 14, wherein alternating optimization includes eigenvalue decomposition and Euclidean projection.

16. The system as recited in claim 10, wherein:
  an individual similarity measure is determined for each expert; and
  the composite distance metric is provided back to each expert to compare to the individual similarity measure.

17. The system as recited in claim 10, wherein a similarity measure between a first patient with a first vector and a second patient with a second vector is determined by computing a Mahalanobis distance between the first vector and the second vector.

18. The system as recited in claim 10, wherein the data distribution includes at least one of a multilinear data distribution and a nonlinear data distribution.

19. The system as recited in claim 10, wherein the data distribution is a nonlinear data distribution.

20. A computer readable storage medium comprising a computer readable program, wherein the computer readable program when executed on a computer causes the computer to perform the steps of:
  converting base distance metrics from a plurality of sources into neighborhoods for comparison, wherein each base distance metric represents an expert; and
  combining the neighborhoods to leverage the local discriminalities of all base distance metrics by applying at least one iterative process to output a composite distance metric.

* * * * *